United States Patent [19]
Hwang et al.

[11] Patent Number: 5,986,002
[45] Date of Patent: Nov. 16, 1999

[54] MEDICAL ARTICLE OF IMPROVED STERILIZABILITY

[75] Inventors: Chorng-Fure Robin Hwang, Cary; Christopher John Knors, Raleigh; Joel L. Williams, Cary, all of N.C.

[73] Assignee: Becton, Dickinson and Company, Franklin Lakes, N.J.

[21] Appl. No.: 08/985,895

[22] Filed: Dec. 5, 1997

[51] Int. Cl.$^6$ ...................................................... C08F 8/00
[52] U.S. Cl. ...................... 525/101; 604/256; 525/193; 525/288
[58] Field of Search .................................. 525/101, 193, 525/288; 520/248, 310, 312; 560/163, 221; 562/439; 564/164; 604/256

[56] References Cited

U.S. PATENT DOCUMENTS

| | | | |
|---|---|---|---|
| 5,142,010 | 8/1992 | Olstein | 526/248 |
| 5,741,858 | 4/1998 | Brenn et al. | 525/101 |

FOREIGN PATENT DOCUMENTS 0 702 032 A2  3/1996  European Pat. Off. .

*Primary Examiner*—Corrine McDermott
*Assistant Examiner*—Kent Gring
*Attorney, Agent, or Firm*—Richard E. Brown

[57] ABSTRACT

A medical article is molded from a silane-grafted polyolefin copolymer and crosslinked to have improved compression set and sealability so that the crosslinked article can be sterilized with substantially no changes in size or shape.

7 Claims, 7 Drawing Sheets

MEDICAL ARTICLE OF IMPROVED STERILIZABILITY

FIELD OF THE INVENTION

This invention relates to medical articles, and more particularly relates to medical articles of improved sterilizability resulting from improved physical properties.

BACKGROUND

Medical articles are conventionally made by thermoplastic processing of polyolefins or copolymers thereof. Typical plastics used are polyethylene, polypropylene or copolymers of these materials with one or more other monomers such as styrene, acrylic or butadiene. A variety of physical properties can be achieved according to the medical application envisioned for the plastic.

One important criterion to be considered when selecting a plastic for medical application is the morphological stability of the plastic when subjected to physical stress, such as conventional sterilization procedures. Thus, the plastic must not undergo any substantial change in size or shape during sterilization which would compromise the specifications required for proper end use. This is particularly true for multicomponent articles having contiguous parts of close tolerances where avoidance of size changes is very important if sealing contact between the parts must be maintained.

If the sealing components also have a sliding relationship, the phenomenon known as stick-slip is often a problem. Thus, it is well known that two plastic surfaces having a sliding relationship often exhibit sufficient resistance to initiation of sliding movement that gradually increased pressure applied to one of the surface does not cause movement until a threshold pressure is reached at which point a sudden sliding separation of the surfaces takes place. This situation is commonly referred to as stick-slip or sticktion. Stick-slip is exacerbated by prolonged stationary contact between the surfaces, such as occurs during shelf time. It is particularly troublesome in devices such as syringes, in particular syringes to be used with syringe pumps where ultra slow advancement of the stopper is required, and repeating sequential episodes of stick-slip occurs. The term tribology refers to the study of friction, lubrication and wear of surfaces in relative motion.

Natural rubber has been fabricated into articles of low stick-slip which resist morphological change because of low compression set. This material is, however, expensive, difficult to process and for this reason, SANTOPRENE™ (blend of polypropylene and EPDM (ethylene-propylenediene monomer) has become a material of choice for stoppers intended for medical use. This material, while of excellent compression set, is subject to substantial stick-slip.

It is toward provision of articles, particularly multicomponent medical articles of improved set and seal retention and minimal stick-slip that the present invention is directed.

SUMMARY OF THE INVENTION

A silane grafted copolymer (SGC) of ethylene and an alpha olefin having 3–20 carbon atoms having particular hardness, density and melt flow index is molded to the shape of a medical article and treated with water to give a crosslinked silane-grafted copolymer (CSGC). Preferred medical articles have a plurality of components. The most preferred articles are tube closure assemblies and syringe assemblies. Preferred alpha olefins have 4 to 8 carbon atoms and 0.1 to 10 weight percent of grafted silane groups pendant to the polyolefin chains.

The CSGC of the invention has very low compression set making it particularly suitable for articles which must be sterilized. The low set enables the article to undergo autoclave conditions with minimal morphological changes so that tolerance specifications between parts in a contiguous or sliding relationship are not compromised and leakage between the parts does not develop. When used as one component of a multicomponent article, substantially no stick-slip occurs.

DETAILED DESCRIPTION

While this invention is satisfied by embodiments in many different forms, there will herein be described in detail embodiments of the invention with the understanding that the present disclosure is to be considered as exemplary of the principles of the invention and is not intended to limit the invention to the embodiments illustrated and described. The scope of the invention will be measured by the appended claims and their equivalents.

The medical article contemplated by the invention to benefit from the improved compression set and seal retention exhibited by the disclosed CSGC may be, for example, shields, syringe and tube stoppers and the like, where close tolerances between a needle and shield or between a stopper and a tube or septum therein must be maintained during conventional sterilization by autoclaving, ethylene oxide or radiation. Preferred medical articles are multicomponent articles, at least one component of which comprises the CSGC, such as tube closure assemblies in which sealability between a stopper or cap portion of the CSGC and a septum is maintained. The closure assembly may include an optional permeability lowering barrier adjacent the septum. The most preferred medical article is a syringe assembly, either 2-piece or 3-piece, in which the sliding seal between a stopper of CSGC and a barrel remains uncompromised and free of stick-slip during sterilization or use. For both the syringe assembly and the closure assembly having a stopper of CSGC, other components, such as barrel, plunger rod and septum respectively, may be of glass or any suitable elastomer. The invention will henceforth be described for the syringe and closure assemblies with the understanding that the description thereof may equally well be applied to other medical articles which would benefit from the outstanding compression set and sealability provided by the composition disclosed.

Figure 1:
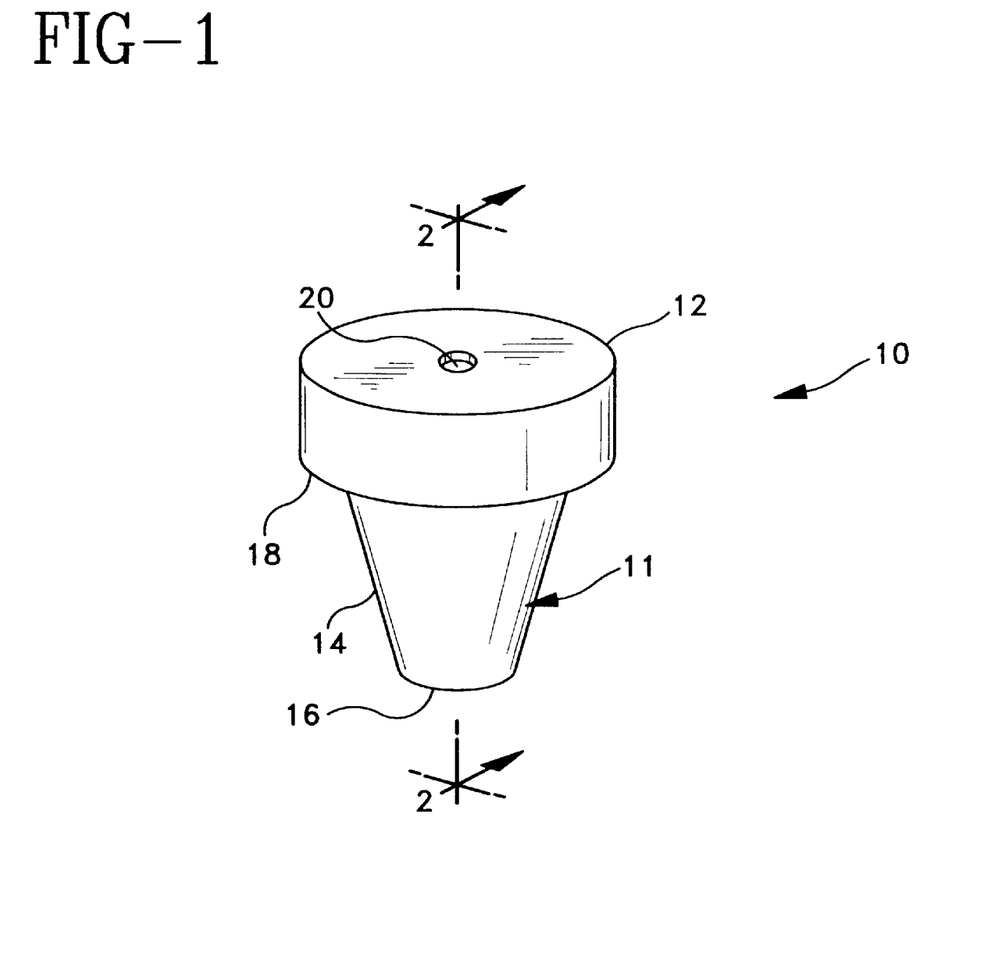
FIG. 1 is a perspective view of the closure assembly of the invention.
Figure 2:
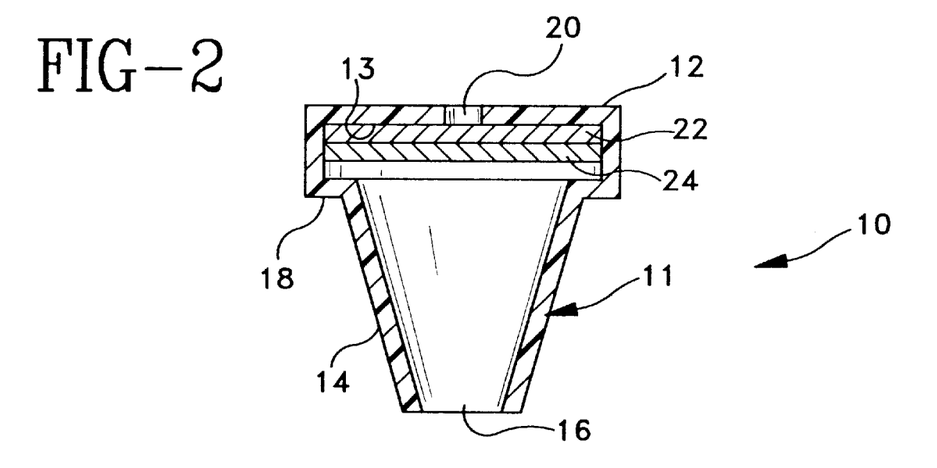
FIG. 2 is a vertical sectional view of the assembly of Claim 1 taken along the line 2—2 thereof.
Figure 3:
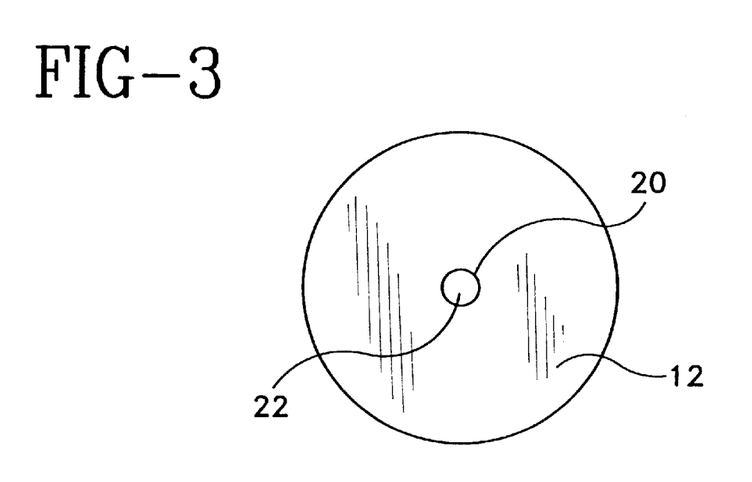
FIG. 3 is a top plan view of the assembly of Claim 1.

Adverting now to the drawings, FIGS. 1–3 illustrate a typical closure assembly of the invention. Assembly 10 includes a cap portion 11 having an annular top wall 12 with a bottom edge 13 and a side wall 14 defining an open bottom end 16. Side wall 14 may include a shelf 18 for engagement with the lip of a tube (not shown). Top wall 12 includes an opening 20 to receive a needle. A conventional septum 22 is adjacent and adhered to bottom edge 13 of cap portion 11. A permeability lowering barrier 24, preferably of foil, is adjacent and adhered to septum 22. As shown in FIG. 3, septum 22 is visible through opening 20 when the closure assembly is viewed from above.

The septum may be of any suitable elastomer as known in the art, and the barrier is preferably of foil, such as aluminum foil.

Figure 4:
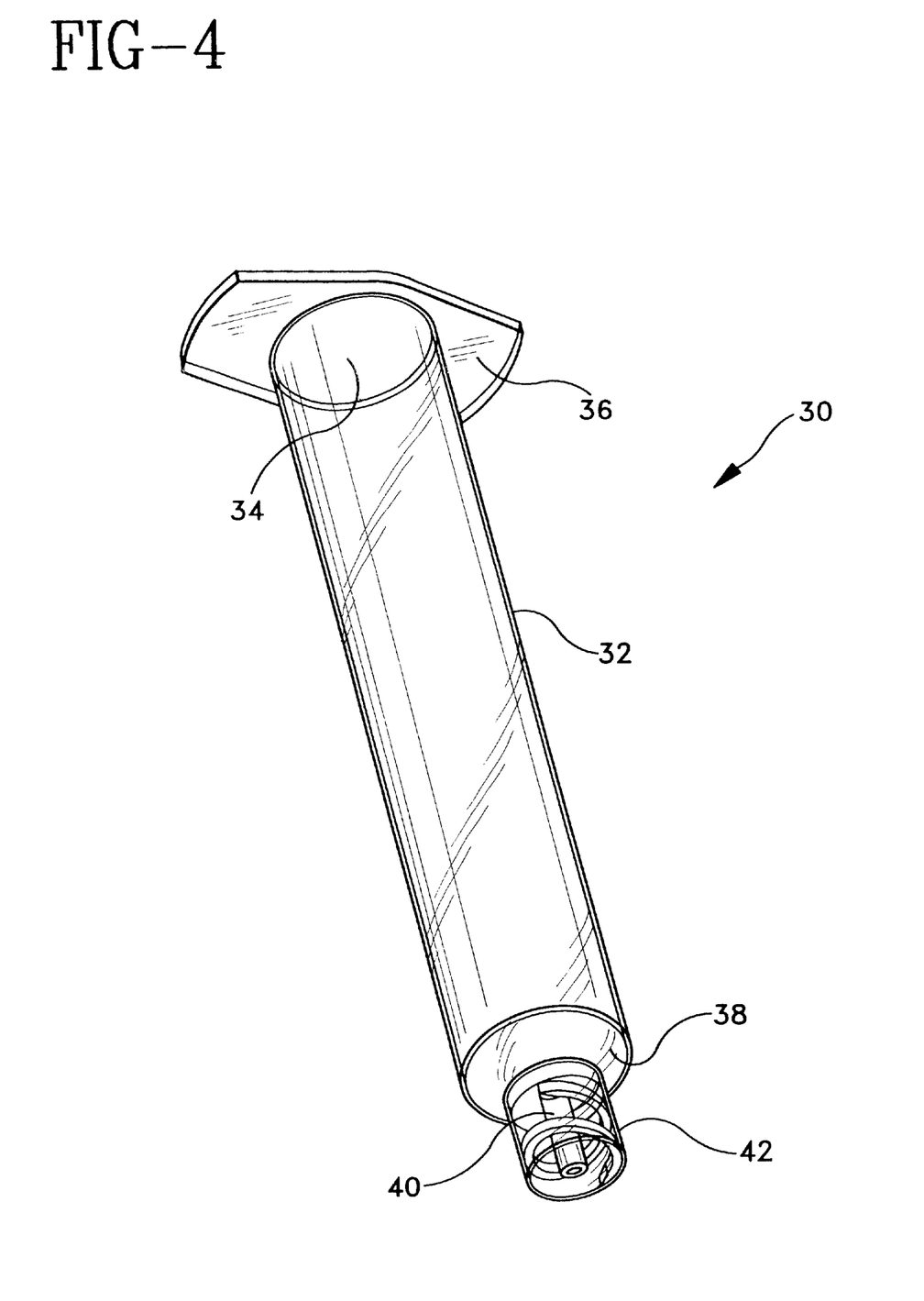
FIGS. 4–6 are perspective views of a syringe barrel and two syringe stoppers of the syringe assembly of the invention.
Figure 5:
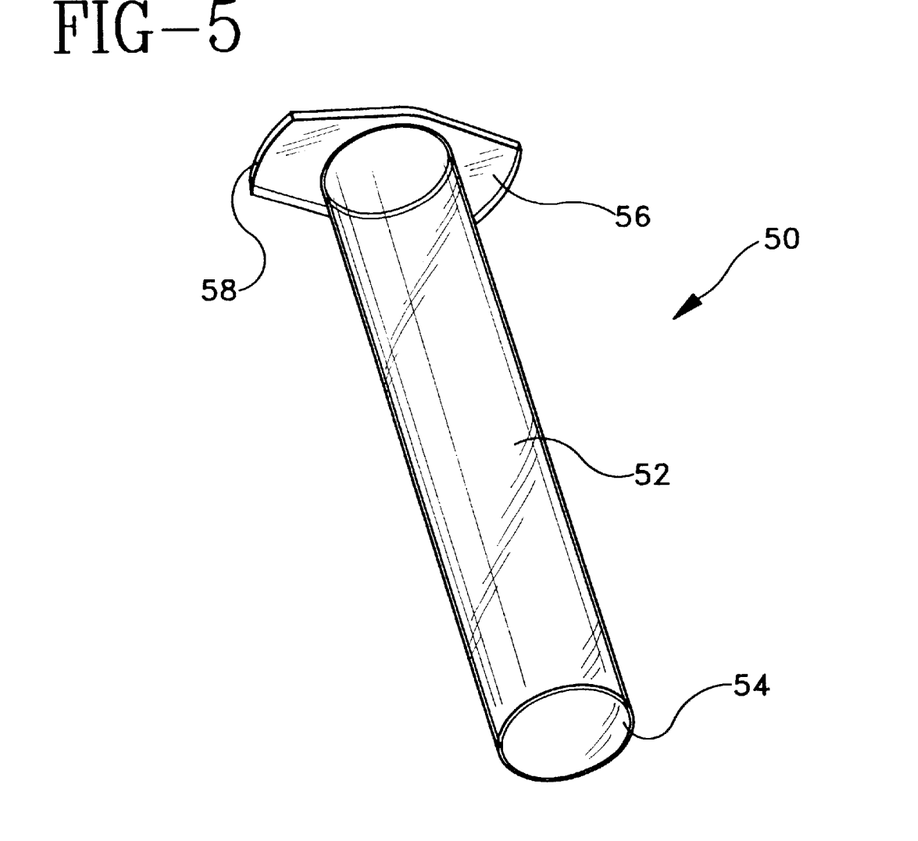

FIGS. 4 and 5 illustrate a typical syringe stopper and barrel assembly. In FIG. 4, syringe barrel 30 has a body portion 32 having an open top end 34, an inside wall 35 and an optional grasping portion 36. A bottom wall 38 includes a tube portion 40 for delivery of a fluid from body portion 32 when the assembly is in use. Bottom portion 38 is affixed to a conventional hub 42.

In FIG. 5, a syringe stopper 50 for a 2-piece assembly has a body portion 52 and a bottom wall 54. A top wall 56 has an annular projection 58 so that, when the assembly is in use, the stopper can be advanced and retracted in the barrel. Stopper 50 is dimensioned to have a sliding and sealing relationship to inside wall surface 35 of body portion 32 of barrel 30.

Figure 6:
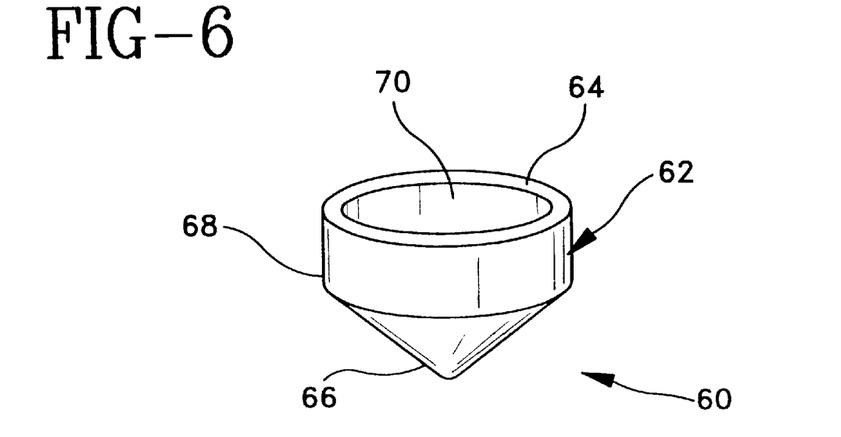

FIG. 6 illustrates a stopper 60 adapted to be mounted on a conventional plunger rod of a 3-piece syringe assembly. Stopper 60 may have a body portion 62 having a top wall 64, a bottom wall 66 and a side wall 68. Body portion 62 has a recess 70 into which the plunger rod (not shown) is securely mounted. The rod-stopper assembly is inserted into the barrel so that the stopper slides sealingly against the inside wall of the barrel.

A conventional lubricant, such as polydimethylsiloxane (not shown in the drawings) may be present between the stopper and barrel.

The compositions found to have the improved compression set and seal capability advantageous for medical articles may generally be described as thermoplastic elastomers (TPE), preferably crosslinked polyolefins. Polyolefins suitable for crosslinking are copolymers of ethylene with an alpha olefin having 3–20, preferably 4–8 carbon atoms. Most preferably, the copolymers are members of the class known in the art as plastomers, i.e., polymers or copolymers made using metallocene catalysts. Ethylene-alpha olefin copolymers which have been found to be suitable for processing and crosslinking as described below are commercially available from Aldrich Chemical Co. from Exxon under the trade name EXACT™ or from Dow under the trade name ENGAGE™.

In preparation for processing and crosslinking, the copolymers may be grafted to silane groups to give the SGC. Silane crosslinking reagents are sold by HULS AG, Somerset, N.J., under the trade name DYNASYLAN™. While not wishing to be limited thereby, a preferred crosslinking agent is vinyl trimethoxysilane which grafts onto a polyolefin chain under catalysis by peroxide. Preferably, about 0.1 to 10% by weight, most preferably about 2–10%, of reactive silane groups are grafted onto the polyolefin. Preferred SGC have a density of 0.85 to 0.95 most preferably 0.85–0.87 g/cc, a melt flow index of 0.1 to 1000, preferably 1 to 100 dg/10 min, a durometer hardness of 40–70 A and a molecular weight distribution of 2–5, preferably about 3. Silane crosslinking technology is well known in the art, and further details on this aspect of the invention are not needed for a complete understanding of the invention by one skilled in the polymer arts.

Other additives as known in the art may be added prior to or subsequent to grafting to provide other desirable properties. For example, fillers, clarifying agents, coloring agents, radiation stabilizers, antistatic materials, wetting agents, oils to reduce hardness, catalysts, foaming agents and the like may be added in suitable quantities. One skilled in the art of polymer compositions is well versed in such additives and no further description of these materials is needed for a complete understanding of the invention.

The SGC may be processed by any convenient technique such as injection, compression or rotary compression molding to have the shape of a medical article. The shaped article may then be exposed to moisture whereby the grafted silane groups react to crosslink the polymer molecules through siloxane groups (to form the CSGC). The shaped article may be immersed in a water bath at any temperature from 1 to 100° C. for about 1 minute to 16 hours, or preferably may simply be exposed to steam or an atmosphere of high water vapor content until crosslinking is complete.

Alternatively, the SGC in molten form may be crosslinked by moisture, and while still molten, the resulting CSGC may be processed into the desired shape.

In accordance with the invention, it has been found that the CSGC and articles therefrom have greatly improved compression set, seal retention and stick-slip and are particularly well suited for manufacture of multi-component medical assemblies. The term compression set is used in its conventional sense as a measure of the permanent deformation of a material which has been stressed, i.e. the percentage of compressive deformation not recovered on removal of the stress. Thus, a compression set of 0% indicates that all deformation is recovered and no permanent morphological change has occurred whereas a compression set of 100% indicates no recovery upon removal of the stress.

As applied to the medical articles of this invention, the improved compression set of the CSGC provides the advantage of minimal change in morphology of the shaped medical article when subjected to stress, such as sterilization conditions. In particular, it has been found that articles of the invention have compression set of less that 20% after autoclaving. Compression set may be measured in accordance with ASTM D395. Set data is given in the Table for syringe stoppers of CSGC and several prior art plastics in a polypropylene barrel.

In order to develop a leak-free seal between, for example, a plastic syringe stopper in a barrel, it is conventional to manufacture the stopper OD larger than the barrel ID in order to develop a strain between the components. It is however, well known that plastics tend to creep during autoclaving or during shelf time. Creep can reduce the strain and compromise the seal.

In accordance with the invention, seal retention in a syringe assembly depends on retention of the strain imparted at the stopper-barrel interface during sterilization and autoclaving. Strain may be determined by the procedure of Example 1. It has been found that a leak-free seal between a syringe stopper of the CSGC and a polypropylene syringe barrel may be achieved if a strain of 3% or more is retained after autoclaving. Minimum strain providing leak-proof seals after radiation sterilization and subsequent autoclaving is given in the Table for stoppers of the polyolefin copolymer, the CSGC of the invention and for two plastics commonly used in prior art syringe stoppers.

Figure 7:
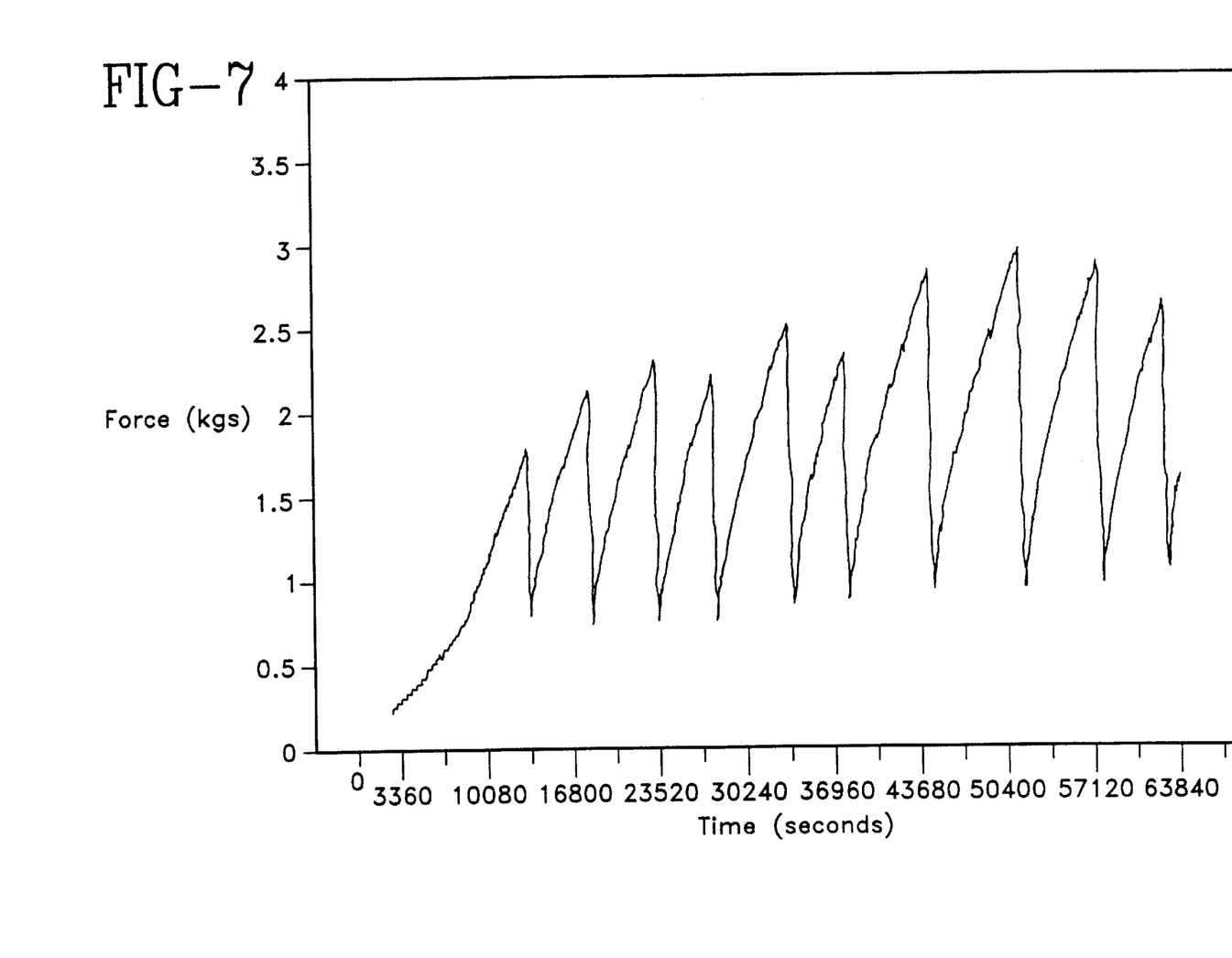
FIGS. 7–9 are plots illustrating stick-slip for syringe assemblies including barrels of the CSGC of the invention and two prior art barrels respectively.
Figure 8:
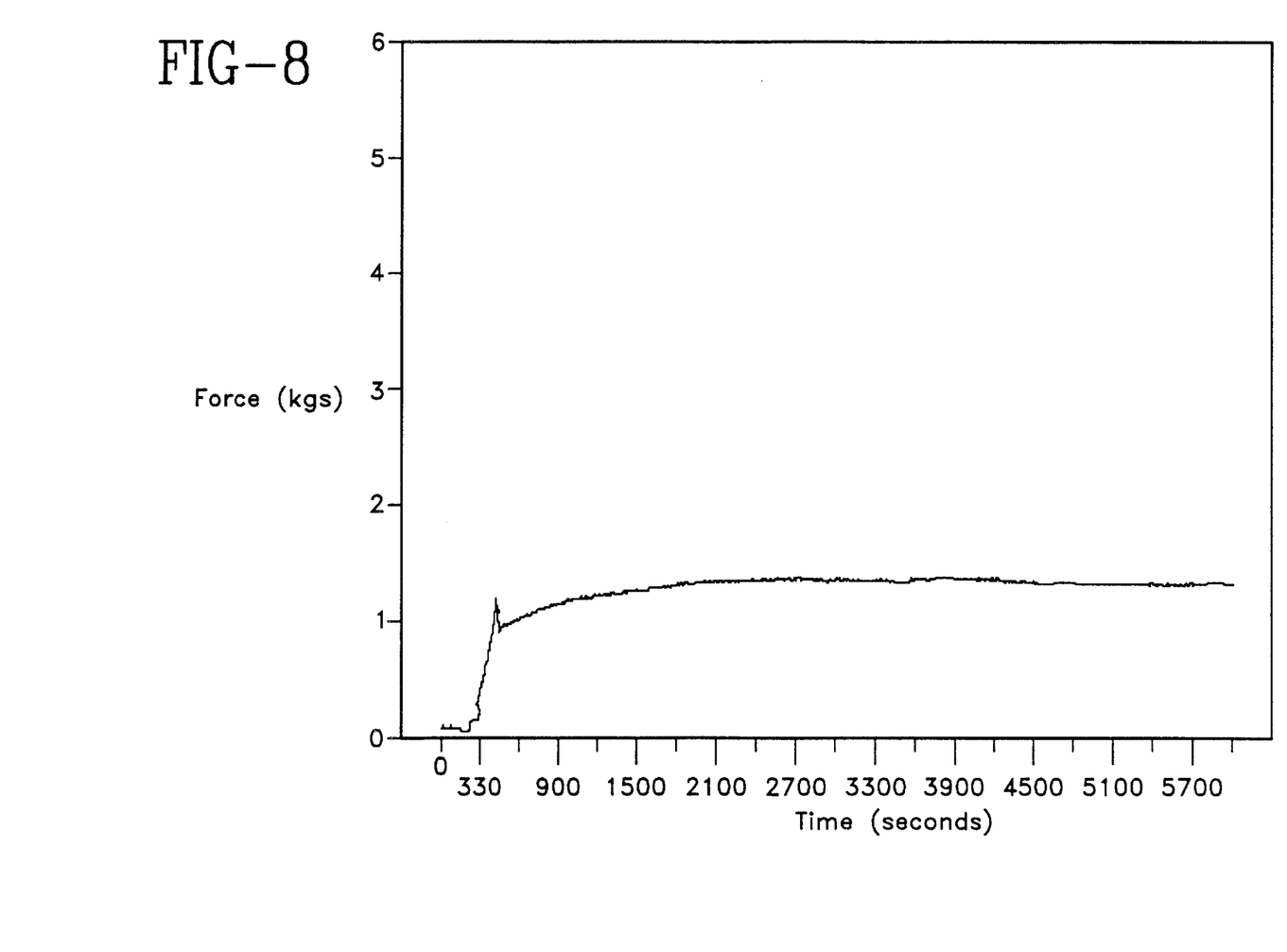
Figure 9:
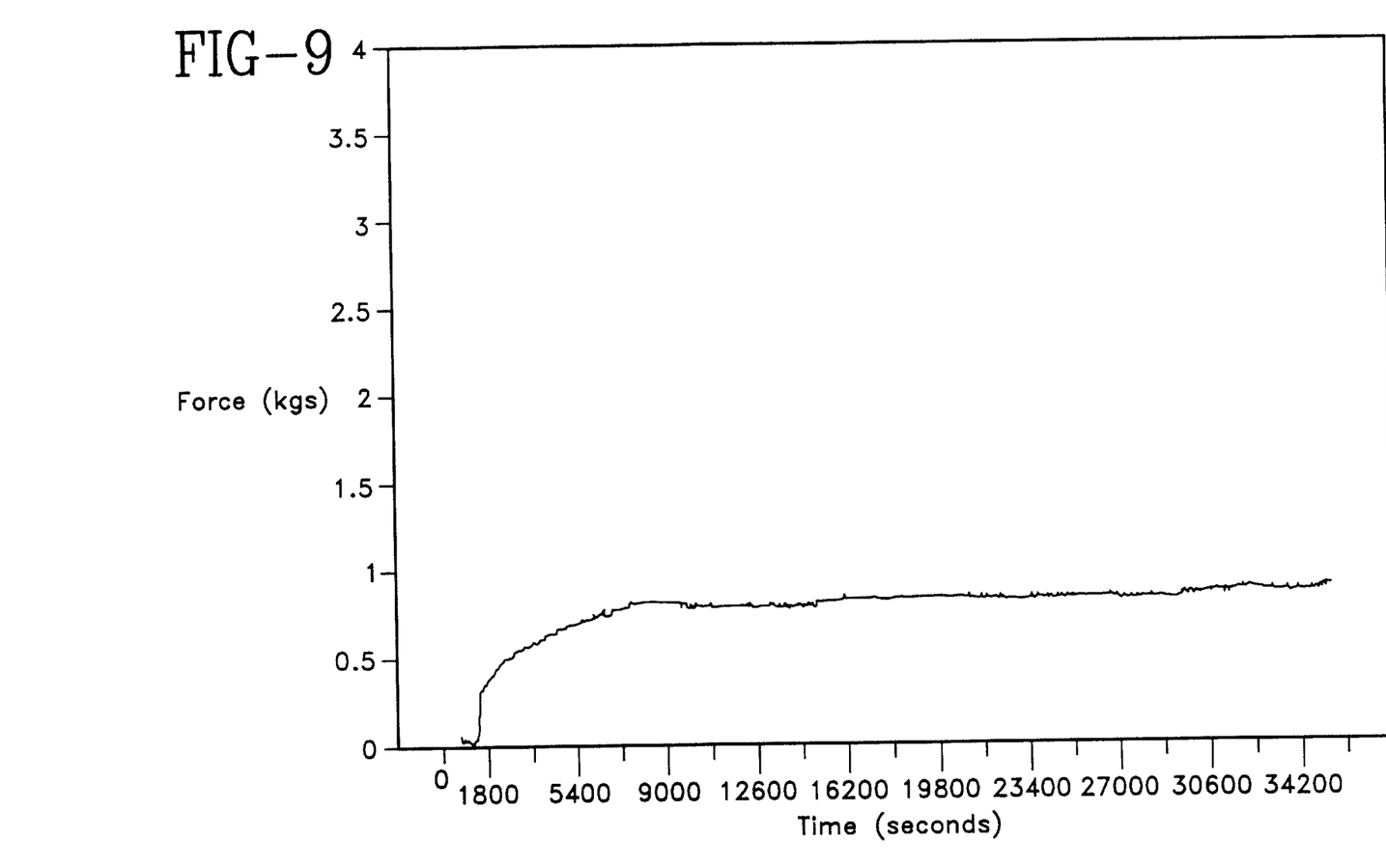

In addition to having improved compression set and strain retention, the article of the invention provides excellent tribological properties when tested by the procedure of Example 2. It has been found that the syringe stopper described above and fabricated from the CSGC of the invention slides smoothly in a conventional syringe barrel with substantially no stick-slip. FIGS. 7 and 8 show the smooth advancement of syringe stoppers of CSGC and natural rubber respectively in polypropylene syringe barrels. FIG. 9 illustrates severe stick-slip which occurs when a stopper of SANTOPRENE™ is advanced in a polypropylene barrel.

TABLE

| TPE | SET[a] | STRAIN % | | |
|---|---|---|---|---|
| | | Initial | Radiation | AUTOCLAVE[a] |
| EXACT, ENGAGE | 100 | 37.0 | 0.0 | |
| SANTOPRENE[b] | 20 | 28.3 | 22.1 | 6.6 |
| natural rubber[c] | 10 | 27.0 | 19.0 | 9.4 |
| CSGC | 8 | 32.9 | 22.8 | 3.0 |

[a]autoclaved at 131° C., 15 min.
[b]AES Corp, Akron, Ohio
[c]Wesr 568B; West Rubber Co.

The experimental data establish that multicomponent assemblies having a component of the CSGC are improved over prior art articles of the hitherto plastics of choice. It is seen from the Table that the compression set and strain retention of the CSGC are comparable, after radiation and autoclaving, to that of SANTOPRENE™ and natural rubber, the two most commonly used prior art plastics for syringe and closure components. However, SANTOPRENE™ fails the stick-slip test. Natural rubber, while satisfactory with respect to compression set, strain retention and stick-slip, is more expensive and more difficult to fabricate.

EXPERIMENTAL

EXAMPLE 1

Measurement of Strain

The following measurements were made to an accuracy of 0.0001 in. (0.000254 cm):

1) barrel ID was measured with a spit-ball gauge (Mitatoyo Corp., Model 1DC-112CE, Tokyo, Japan);
2) plunger rod OD was measured at the stopper connection point with a comparator (Optical Gaging Products, Model SSFOV2OO, Rochester, N.Y.);
3) stopper ID was measured by casting a mold of the inside of the stopper (FIG. 6, reference numeral 70) using a curable RTV silicone (GE Silicones Corp, RTV88, Norcross, Ga.), removing the cured plug and measuring its OD using the comparator.
4) stopper OD was measured after being affixed to the plunger rod. Initial strain was calculated with Equation I:

EQUATION I
strain=interference stopper OD-stopper ID
where interference=(stopper OD-barrel ID+(plunger rod OD-stopper ID)

B Strain After Sterilization:

The stopper-plunger rod assembly was inserted into the barrel and sterilized (gamma, e-beam or EtO) and strain after sterilization calculated with Equation II:

EQUATION II
strain=interference Stopper OD
where interference=stopper OD-barrel ID C Strain After Sterilization and Autoclaving (131° C.; 15 min) was calculated with equation II.

EXAMPLE 2

Measurement of Stick-Slip

A 60 ml syringe having a barrel and stopper was mounted onto a syringe pump fitted with a force transducer which grips the thumbpress of the stopper. The transducer was calibrated to the "O" line on the monitor of a computerized data acquisition system and the syringe barrel filled with deionized water and purged of air bubbles. The pump was set for the slowest possible speed (0.1 ml/hr) to give maximum stick-slip. Force data against time was collected at the monitor. FIG. 7 shows substantial stick-slip for a SANTOPRENE™ stopper. FIG. 8 shows relatively little stick-slip for the stopper of the invention, as does FIG. 9 for a natural rubber stopper.

What is claimed is:

1. A medical article comprising a first component of a crosslinked silane-grafted copolymer of ethylene and an alpha olefin of 3 to 20 carbon atoms, said copolymer having a durometer hardness of 40 to 70 A, a density of 0.85–0.95 g/cc and a melt flow index of 0.1–1000 dg/10 min, and a second elastomeric component sealingly engaged to said first component.

2. The article of claim 1 which is a closure assembly wherein said first component is a cap portion and said second component is an elastomeric septum portion.

3. The article of claim 1 which is a syringe assembly wherein said first component is a stopper portion and said second component is a barrel portion for receiving said stopper in sealing engagement, said stopper portion sliding in said barrel portion with substantially no stick-slip.

4. A tube closure assembly comprising:
   a) a molded cap of a crosslinked silane-grafted copolymer of ethylene and an alpha olefin of 3 to 20 carbon atoms, said copolymer having a durometer hardness of 40–70 A, a density of 0.85 to 0.95 g/cc and a melt flow index of 0.1 to 1000 dg/10 min, said molded cap having a wall portion and a top portion defining an opening;
   b) an elastomeric septum covering said opening and sealably adhered to said top wall; and
   c) a permeability lowering barrier affixed to said septum.

5. A syringe assembly comprising:
   a) a molded stopper of a crosslinked silane grafted copolymer of ethylene and an alpha olefin having from 4 to 8 carbon atoms, said copolymer having a durometer hardness of 40–70 Shore A, a density of 0.85 to 0.95 g/cc and a melt flow index of 1 to 100 dg/10 min;
   b) an elastomeric syringe barrel dimensioned to receive said stopper in sliding and sealing engagement; and
   c) a plunger rod having said stopper adhered thereto, said stopper portion sliding in said barrel portion with substantially no stick-slip.

6. A method to make a syringe assembly comprising:
   a) molding a silane grafted copolymer of ethylene and an alpha olefin of 3 to 20 carbon atoms into the shape of a syringe stopper, said copolymer having a durometer hardness of 40 to 70 A, a density of 0.85–0.95 g/cc, and a melt flow index of 0.1–1000 dg per 10 min;
   b) crosslinking said copolymer; and
   c) inserting the stopper after crosslinking into a syringe barrel.

7. The method of claim 6 wherein said stopper after crosslinking is mounted onto a plunger rod prior to said inserting step.

* * * * *